United States Patent [19]

Shattuck et al.

[11] Patent Number: 4,591,794
[45] Date of Patent: May 27, 1986

[54] GAS TURBINE ACCESS PORT PLUG ELECTROSTATIC PROBE

[75] Inventors: Alan B. Shattuck, Lake Park; Robert P. Couch, Palm Beach Gardens, both of Fla.

[73] Assignee: United Technologies Corporation, Hartford, Conn.

[21] Appl. No.: 454,113

[22] Filed: Dec. 28, 1982

[51] Int. Cl.[4] .............................................. G01N 27/62
[52] U.S. Cl. .................................. 324/464; 324/72.5; 324/457; 340/627
[58] Field of Search ............... 324/464, 457, 72, 72.5, 324/459, 452, 65 P, 65 CR; 73/861.09; 340/627

[56] References Cited

U.S. PATENT DOCUMENTS 3,447,071  5/1969  Webb ................................... 324/464
3,775,763  11/1973  Couch et al. ......................... 340/627

OTHER PUBLICATIONS

Couch, R. P., "Detecting Abnormal Turbine Engine Deterioration using Electrostatic Methods", Journal of Aircraft, vol. 15, No. 10, Oct. 1978, pp. 692-695.

Primary Examiner—Ernest F. Karlsen
Assistant Examiner—Kevin D. O'Shea
Attorney, Agent, or Firm—M. P. Williams; Gerald E. Linden

[57] ABSTRACT

An electrostatic probe (27) includes seals (47, 54) adapted to engage sealing surfaces of a borescope access hole provided in the inner and outer walls (24, 25) of the fan duct (22) of a gas turbine engine. The probe includes a center conductor (60), the exposed proximal end of which (31) forms an electrode tip, insulated (35, 36) from an outer metallic wall structure (38, 66), the conductor and wall structure terminating in a coaxial connector 64. A latch means (34, 58) cooperates with a lock pin (76) in one of the fan duct walls.

1 Claim, 3 Drawing Figures

GAS TURBINE ACCESS PORT PLUG ELECTROSTATIC PROBE

TECHNICAL FIELD

This invention relates to electrostatic monitoring of gas turbine engines, and more particularly to electrostatic probes which may be readily inserted and removed, or retained during operation while in flight, as desired, in borescope access ports of a gas turbine engine.

BACKGROUND ART

For the past decade, monitoring electrostatic charge in the exhaust gas of a jet engine has been investigated as a possible indication of engine deterioration and/or impending engine failure. As reported in U.S. Pat. No. 3,775,763, it was originally thought that small particles of engine parts, having a net charge, caused spikes of ion current of relatively large magnitude when striking an electrostatic probe. Later, it was theorized that the electrical activity on ionic probes was the result of Trichel pulses (a form of repetitive corona discharge) created by high potential pockets of excess charge, related to engine wear. This is reported by Couch, R. P.: "Detecting Abnormal Turbine Engine Deterioration using Electrostatic Methods", *Journal of Aircraft*, Vol. 15, October 1978, pp 692-695. The apparatus described in said article utilized a probe set including circular insulated segments within the gas turbine engine tail pipe and a triangle of wire extending through the tail pipe exhaust gas path. With these probes, a normalized count of probe current (or voltage developed across an impedance) in excess of a threshold magnitude, over a period of time, was found to definitely correlate to impending engine component malfunctions or severe deterioration. However, the use of normalized counts of large magnitude signals from the ring and grid probe was found to provide reliable prediction of only two out of three gas path failures, at best, and was found to not provide any distinction between possible causes thereof.

In this prior period of time, attempts were made to determine whether or not there were any electrostatic phenomenon observable in other parts of a gas turbine engine which would be of any significance in engine diagnostics. However, no useful signals were found.

Obviously, the usefulness of any diagnostic tool is generally enhanced by the variety and versatility thereof.

DISCLOSURE OF INVENTION

Objects of the invention include provision of means to sense electrostatic phenomenon within the gas stream of a gas turbine engine at other than the tail pipe thereof, and provision of electrostatic probes which are readily inserted in and removed from or retained on the engine, for electrostatic diagnostics thereof.

This invention is predicated in large part on my discovery that there are significant electrostatic phenomena in the gas stream of an engine within the compressor and turbine sections thereof which are useful for electrostatic diagnostics.

According to the present invention, an electrostatic probe is adapted for insertion within the borescope access ports thereof, and includes means to retain the probe in place while the engine is in operation, as well as means to seal any necessary gas paths while inserted within the engine thereby to facilitate use thereof without causing any impairment of engine operation.

The invention may readily be practiced by conversion of access port plugs existing for an engine into electrostatic probes, or by the fabrication of special probe structures, when found to be desirable. Probes in accordance with the invention may be utilized at various stations in the engine, subject only to the availability of access ports therefor. Probes in accordance with the invention may be fabricated utilizing materials and techniques which are well within the skill of the art, in the light of the teachings which follow hereinafter.

The foregoing and other objects, features and advantages of the present invention will become more apparent in the light of the following detailed description of exemplary embodiments thereof, as illustrated in the accompanying drawings.

BEST MODE FOR CARRYING OUT THE INVENTION

Figure 1:
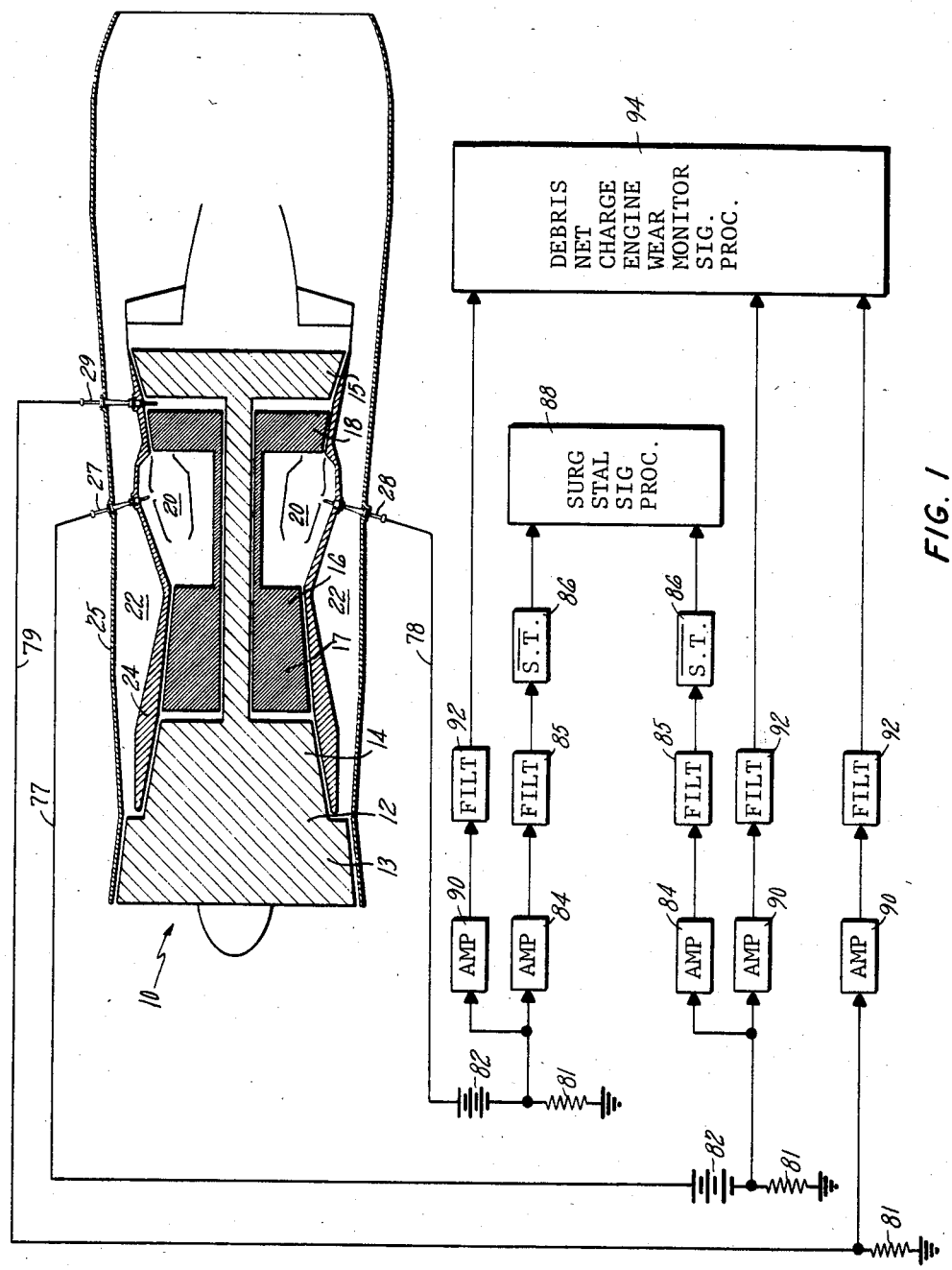
FIG. 1 is a simplified, sectioned side elevation view of a gas turbine engine having electrostatic probes of the present invention disposed therein together with a simplified schematic block diagram of exemplary signal processing apparatus which may be utilized with the probes.

Referring now to FIG. 1, a gas turbine jet engine 10 includes a low pressure spool 12 having a fan 13, a low pressure compressor 14, and a low pressure turbine 15, as well as a high pressure spool 16 including a high pressure compressor 17 and a high pressure turbine 18. An annular burner can or combustor 20 is disposed between the compressors and the turbines. An annular fan duct 22 is defined by inner and outer annular walls thereof 24, 25, respectively. A pair of probes 27, 28 are disposed through the fan duct 22 with their electrode tips in the vicinity of the burner can 20, as is described more fully with respect to FIG. 3, hereinafter. A probe 29 is disposed through the fan duct 22 with its electrode tip extending into a stator portion of the engine between the two turbines 15, 18. The probes 27-29 may take the form illustrated in detail in FIG. 2.

Figure 2:
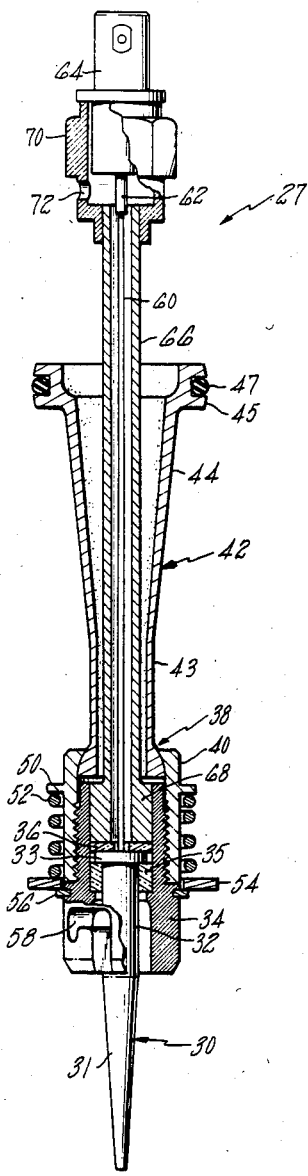
FIG. 2 is a sectioned front elevation view of one embodiment of a probe in accordance with the present invention.

Referring to FIG. 2, the probe 27 has a metallic electrode 30 which includes a tapered tip portion 31, a cylindrical shaft portion 32 and a flange 33 which is supported and insulated from a latch piece 34 by a cylindrical insulator 35 and an insulating washer 36, leaving an annular space between the periphery of the flange 33 and the latch piece 34. The latch piece 34 is threaded into a main housing 38 which may be made of two pieces welded together: a short proximal piece 40 and a long distal piece 42. (As used herein, "proximal" refers to a direction towards the inside of the engine when the probe is in place. "Distal" refers to a direction towards the outside of the engine.) The distal piece 42 has a cylindrical portion 43 and a conical portion 44, as well as an end flange 45 which has a notch therein to receive an O-ring seal 47. The proximal portion 40 has a flange 50 thereon which acts as a keeper for a coil spring 52, the other end of which urges a seal washer 54 toward the probe tip, the washer 54 being held to the latch piece 34 by a split washer 56. The latch piece 34 has a generally L-shaped key slot 58 for engaging with a pin (described with respect to FIG. 3, hereinafter) for securing the probe to the engine.

In FIG. 2, the electrode 30 has a conductive rod 60 welded to the end thereof centrally of the flange 33 to act as a conductor between the electrode 30 and the center conductor 62 (to which it is brazed) of a standard coaxial cable connector 64. A cylindrical metallic outer conductor 66 has an enlarged proximal end 68 which is welded to the latch piece 34. The distal end of the outer conductor 66 is welded to a back shell 70, the other end of which is soft soldered to the coaxial connector 64. Although not shown in FIG. 2, the inner conductor 60 should be covered with a suitable insulative tubing or the like, such as woven fiberglass tubing, to ensure that there is no contact between the inner and outer conductors 60, 66 under adverse conditions of temperature, vibration and shock.

The electrode illustrated in FIG. 2 may be assembled by first welding the center conductor 60 to the flange 33 of the electrode 30. Then the insulator 35, the electrode 30 and the insulator 36 are inserted into the latch piece 34 from the proximal end thereof (from the top as seen in FIG. 2). Then the outer conductor 66 is inserted into the latch piece 34 and welded to it. Then this assembly is threaded into the housing 38. The back shell 70 is then slipped over the outer conductor 66 and allowed to slide along the outer conductor 66 until it contacts the housing 42, thereby exposing the end of the inner conductor 60. The inner conductor 60 is then brazed to the center conductor 62 of the coaxial connector 64. Then the back shell 70 is moved into contact with the coaxial connector 64 and soft-soldered to it as well as being welded to the outer conductor 66, once it is in the position shown in FIG. 2. A hole 72 in the back shell can then be utilized to fill the distal end of the assembly with room temperature vulcanizing rubber, epoxy or the like, simply to seal and stabilize the connector end of the electrode.

Figure 3:
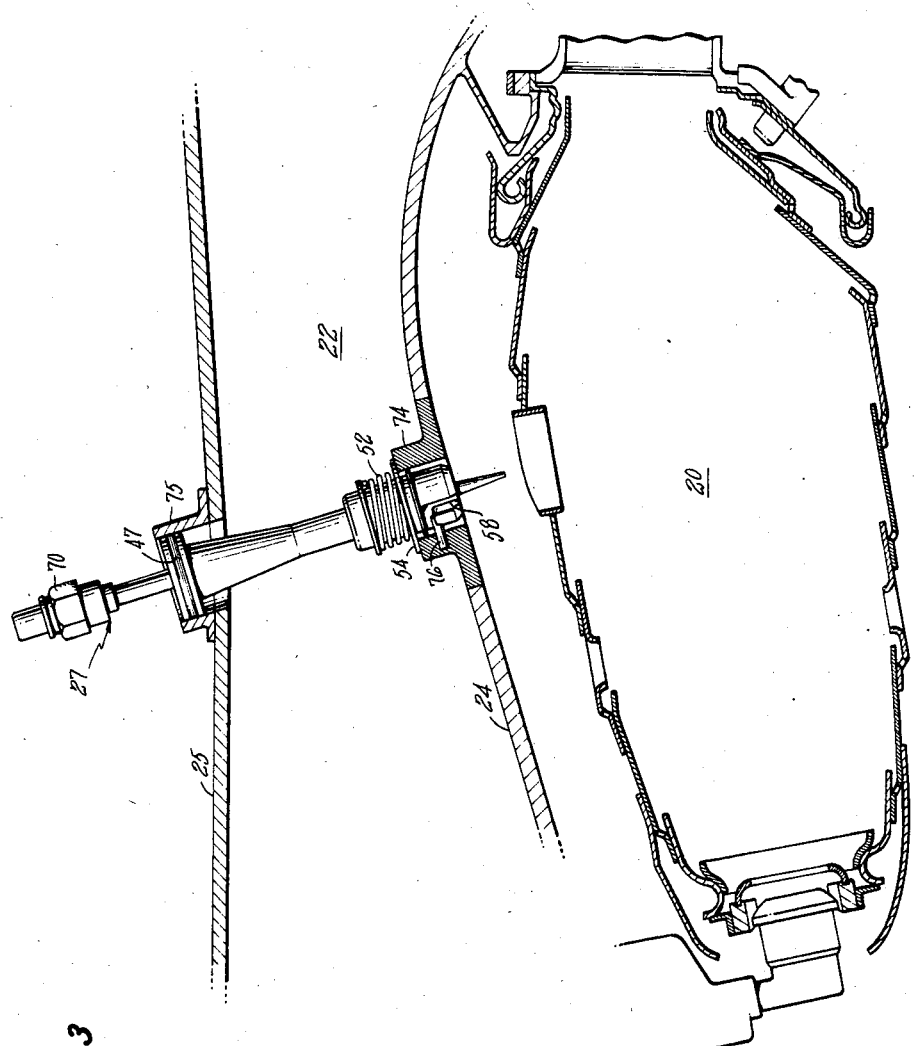
FIG. 3 is a partial, sectioned side elevation view of a portion of a gas turbine engine in the vicinity of a burner can thereof, with a probe according to the present invention inserted in a borescope access hole.

Referring to FIG. 3, the probe 27 is inserted through the inner and outer walls 24, 25 of the fan duct 22. Each of the walls has a corresponding hollow boss 74, 75 disposed thereon. Within the boss 74, a lock means such as a pin 76 engages the generally L-shaped key slot 58: when the probe 27 is inserted, it is aligned so that the pin will slip through the vertical portion of the slot, and then the probe 27 is turned counterclockwise (from the the outside of the engine, the top of FIG. 3) so the pin will engage the horizontal portion of the slot. The hexagonal shape of the back shell facilitates turning the probe into the locked position. As the probe 27 is inserted, the seal washer 54 engages the face of the boss 74 and movement of the probe 27 into the engine causes the spring 52 to compress. This not only provides a suitable seal between the washer 54 and the face of the boss 74, but also causes the pin 76 to remain in the latching bucket of the slot 54, as shown in Fig. 3. The O-ring 47 provides a suitable seal with the interior surface of the boss 75 when the probe is inserted.

Thus the electrostatic probe in accordance with the present invention is easily inserted into the engine by means of the borescope access ports, it provides seals for the gas paths in the engine (such as the fan duct 22) at each end of the probe, and it provides, through the notch 58 and pin 76, means which allow easy insertion and either removal or retention of the probe in the engine.

An alternative embodiment, not shown herein but readily visualized, may eliminate the outer conductor 66 and the distal portion 42 of the housing 38. In their place, high pressure flexible metallic tubing may be utilized. This may take the form of well known tubing which includes an inner, stainless steel bellows tubing surrounded by woven stainless steel mesh. The diameter of the high pressure tubing may be roughly the diameter of the cylindrical portion 43 of the housing 38. The flex tubing may extend all the way from the proximal portion 40 of the housing 38 to the back shell 70, which may also be modified to include a notch for the O-ring seal 47. Utilizing a tube with a larger diameter than the outer conductor 66 facilitates insulating the center conductor 60 from the remainder of the probe by means of room temperature vulcanizing rubber, or epoxy, or the like, since there is adequate clearance for the insertion of such materials. The use of flex tubing is to be preferred in cases where there is differential fore and aft expansion between the inner and outer walls 24, 25 of the fan duct 22, or equivalent structures with which the electrode 27 is in contact. The probe 27 may also be employed with additional members: in the event of difficulty in causing one end of the probe or the other to conform with a mating engine part, adaptor parts can be used, in a manner which is obvious in view of the teachings hereinbefore.

Referring again to FIG. 1, each of the probes 27-29 is connected to signal processing equipment by a suitable corresponding conductor 77-79, which preferably comprises coaxial cables with fittings adapted for engagement with the coaxial connector 64 (FIG. 2). Each of the probes is shown as terminated through a suitable impedance 81, which may typically comprise a resistor of from 50 to 100 kilohms. The probes 27, 28 are shown biased by suitable sources 82 which may be on the order of 60 volts or so in order to sense the presence of ions with no net charge, such as in combustion products which may flow outwardly from the combustor 20 as is described more fully in a commonly owned, copending U.S. patent application entitled "Electrostatic Gas Turbine Surge/Stall Detection", Ser. No. 454,121, filed Dec. 28, 1982 contemporaneously herewith by St. Jacques et al. In such a case, the impedances 81 are connected to amplifiers 84 which feed suitable low pass or band-pass filters 85, the magnitude of the output of which is sensed by Schmidt triggers 86, which are negative level detecting Schmidt triggers in the case of sensing flame. The Schmidt triggers in turn may feed surge/stall signal processing apparatus 88 of the type described in the aforementioned St. Jacques application. The probe 29 is shown unbiased since its presence between the turbines 15, 18 is not for the purpose of sensing flame. Whether the probes 27-29 are biased or not, their impedances 81 may be connected to amplifiers 90, the output of which is applied through filters 92 to an engine wear monitor signal processor 94 which is responsive to the wave shapes of net electrostatic charge resulting from engine debris flowing in the gas stream of the engine, as is described more fully in a commonly owned, copending U.S. patent application entitled "Waveform Discriminated Electrostatic Engine Diagnostics", Ser. No. 454,124, filed Dec. 28, 1982 contemporaneously herewith by Zwicke et al. And, the probes 27-29 may be used in biased and unbiased fashions in more complicated arrangement as described in a commonly owned, copending U.S. patent application entitled "Adaptive Electrostatic Engine Diagnostics", Ser. No. 454,125, filed Dec. 28, 1982 contemporaneously herewith by Rosenbush et al.

The latching mechanism (such as latch piece 34) may, of course, be provided at either end, as suits the needs of any implementation of the present invention. The insulators 35, 36 may be formed of any suitable material, bearing in mind the temperature, vibration and shock which the material may have to withstand. One suitable material is a machinable glass ceramic having a two-phase microstructure of randomly oriented mica crystals in a glass matrix, such as that which is available under the trade name "MACOR" from Corning Glass Works, Corning, N.Y., U.S.A. The insulators 35, 36, the latch piece 34 and the electrode 30 may all be cemented together with cured SP-1 ceramic cement, or the like, if desired. If "MACOR" is used, it may have threads machined thereon; the latch piece 34 and insulators 35 and 36 may therefore be threaded together and then cemented with SP-1 cement. Also, "MACOR" can be brazed; thus the insulators may be brazed to the latch piece 34 with Ticusil (Titanium/Copper/Silver alloy), if desired. The complex structure of the probe 27 illustrated in FIG. 2 facilitates provision of the seals 47, 54 separately from the joining of the outer conductor portion of the coaxial cable connector 64 by means of the outer conductor 66. Thus, the outer conductor 66 and housing 38 form a composite wall structure that both seals the probe 27 to the sealing surfaces of the fan duct walls and provides ready connection with the outer conductor of the connector 64. On the other hand, simpler structures may be employed. The metallic portions of the electrode may be formed of suitable material, such as Hastaloy X or 347 Stainless Steel, or the like.

Thus, although the invention has been shown and described with respect to exemplary embodiments thereof, it should be understood by those skilled in the art that the foregoing and various other changes, omissions and additions may be made therein and thereto, without departing from the spirit and the scope of the invention.

We claim:

1. An electrostatic probe for detecting ions in a gas path of a gas turbine engine having a fan duct with a borescope access port through inner and outer walls thereof, said port including gas seal surfaces in the inner and outer walls of the fan duct and lock means in one of said fan duct walls for engaging a plug for closing off said port, comprising:

a hollow metallic wall structure including a respective seal for interfacing with each of said gas seal surfaces and latch means cooperating with said lock means to hold said wall structure in place with said respective seals engaging said seal surfaces and with a proximal end of said wall structure adjacent the inner fan duct wall;

a central conductor disposed within and extending beyond the proximal end of said wall structure, the proximal end of said central conductor forming an exposed electrode tip;

an outer cylindrical conductor disposed within and extending beyond the distal end of said wall structure, electrical insulating material disposed between said central conductor and said outer cylindrical conductor to support said central conductor in electrical isolation within said outer cylindrical conductor; and a coaxial cable connector, the outer conductor of which is connected to the distal end of said outer cylindrical conductor and the inner conductor of which is connected to the distal end of said central conductor.

* * * * *